United States Patent

(12) United States Patent
Graham et al.

(10) Patent No.: US 7,972,278 B2
(45) Date of Patent: Jul. 5, 2011

(54) METHOD AND APPARATUS FOR OBJECTIVE ELECTROPHYSIOLOGICAL ASSESSMENT OF VISUAL FUNCTION

(75) Inventors: Stuart L. Graham, West Pymble (AU); Iouri Malov, Turramurra (AU); Alex Kozlovski, Mt Colah (AU); Alexander Klistorner, Mt Colah (AU)

(73) Assignee: The University of Sydney, NSW (AU)

( * ) Notice: Subject to any disclaimer, the term of this patent is extended or adjusted under 35 U.S.C. 154(b) by 130 days.

(21) Appl. No.: 12/253,331

(22) Filed: Oct. 17, 2008

(65) Prior Publication Data
US 2009/0076406 A1  Mar. 19, 2009

Related U.S. Application Data

(62) Division of application No. 10/257,565, filed as application No. PCT/AU01/00423 on Apr. 12, 2001, now Pat. No. 7,740,592.

(30) Foreign Application Priority Data

Apr. 17, 2000  (AU) .................................. PQ6940
Dec. 8, 2000  (AU) .................................. PR1982

(51) Int. Cl.
*A61B 13/00* (2006.01)
*A61B 5/04* (2006.01)
*A61B 5/103* (2006.01)
*A61B 5/117* (2006.01)
(52) U.S. Cl. .................. 600/558; 600/544; 600/587
(58) Field of Classification Search .................. 600/558, 600/372, 382, 383, 544, 587; 351/203, 205; 348/68
See application file for complete search history.

(56) References Cited

U.S. PATENT DOCUMENTS

| 4,255,023 A | | 3/1981 | House .............................. 351/24 |
| 4,320,768 A | | 3/1982 | Ledley et al. .................. 128/733 |
| 4,493,539 A | | 1/1985 | Cannon, Jr. .................... 351/205 |
| 4,697,598 A | * | 10/1987 | Bernard et al. ............... 600/544 |
| 4,736,751 A | * | 4/1988 | Gevins et al. ................. 600/545 |
| 4,832,480 A | | 5/1989 | Kornacker et al. ............ 351/246 |

(Continued)

FOREIGN PATENT DOCUMENTS

DE  4301483  8/1994

(Continued)

OTHER PUBLICATIONS

English Abstract of DE 430 1483 Dated Aug. 11, 1994.

(Continued)

*Primary Examiner* — Jeffrey G Hoekstra
(74) *Attorney, Agent, or Firm* — Ladas & Parry LLP

(57) ABSTRACT

For electrophysiological assessment of visual function using a head mounted stereo display (e.g. virtual reality goggles) for displaying a stimulus which is used to generate a retinal or cortical response. In particular, a method for objective electrophysiological assessment of visual function of at least one eye of a subject includes presenting a visual stimulus to at least one eye of the subject, recording at least one of a retinal response and, a cortical response generated as a result of the presenting; analyzing said response and, as a result of said analyzing, forming a map of the visual function of the at least one eye of the subject6. The invention also relates to as system for such electrophysiological assessment.

7 Claims, 8 Drawing Sheets

U.S. PATENT DOCUMENTS

| | | | | |
|---|---|---|---|---|
| 4,846,567 A * | 7/1989 | Sutter | | 351/224 |
| 4,861,154 A | 8/1989 | Sherwin et al. | | |
| 4,955,389 A | 9/1990 | Schneider | | 128/731 |
| 5,458,117 A | 10/1995 | Chamoun et al. | | 128/734 |
| 5,609,158 A | 3/1997 | Chan | | 128/705 |
| 5,844,824 A | 12/1998 | Newman et al. | | |
| 6,044,292 A | 3/2000 | Heyrend et al. | | 600/544 |
| 6,260,970 B1 * | 7/2001 | Horn | | 351/246 |
| 6,315,414 B1 * | 11/2001 | Maddess et al. | | 351/246 |
| 6,364,845 B1 * | 4/2002 | Duffy et al. | | 600/558 |
| 6,966,650 B2 * | 11/2005 | Hu et al. | | 351/205 |
| 7,220,000 B2 * | 5/2007 | Alster et al. | | 351/224 |
| 7,275,830 B2 * | 10/2007 | Alster et al. | | 351/223 |
| 7,384,145 B2 * | 6/2008 | Hetling et al. | | 351/219 |
| 7,645,140 B2 * | 1/2010 | Duffy et al. | | 434/236 |
| 7,665,847 B2 * | 2/2010 | Alster et al. | | 351/224 |
| 7,682,021 B2 * | 3/2010 | Sabel | | 351/203 |

FOREIGN PATENT DOCUMENTS

| | | |
|---|---|---|
| WO | 9934727 | 7/1999 |
| WO | 9958046 | 11/1999 |

OTHER PUBLICATIONS

Brigatti L., et al., "Virtual Perimetry" 1 1,16 Novel Perimetric Technique Investigative Ophthalmology and Visual Science, Vo. 38, No. 4 Part 1-2, 1997, p. S572 XP008027165 Annual Meeting of Meeting of the Association for Research in Vision and Ophthalmology, Parts 1-2; Fort Lauderdale, Florida, USA; May 11-16, 1997 ISSN: 0146-0404.

Shimoyama et al., Normalized Wave Energy For Background Activity In Visual Evoked Potentials, vol. 24, Nos. 1 & 2, 1998.

* cited by examiner

METHOD AND APPARATUS FOR OBJECTIVE ELECTROPHYSIOLOGICAL ASSESSMENT OF VISUAL FUNCTION

This application is a divisional of application Ser. No. 10/257,565 filed on Feb. 25, 2003 now U.S. Pat. No. 7,740,592, which is a 371 International Application No.: AU2001/000423 filed on Apr. 12, 2001, which designated the U.S., claims the benefit thereof and incorporates the same by reference.

TECHNICAL FIELD

This invention relates to the electrophysiological assessment of visual function using a head mounted stereo display (eg virtual reality goggles) for displaying a stimulus which is used to generate a retinal or cortical response. In particular, the integrity of the visual field can be assessed objectively by measuring retinal or cortical responses to a multifocal visual stimulus presented by a head mounted virtual reality display instead of a conventional monitor. This provides advantages of space, patient acceptance, standardising distance to the display, and the possibility of monocular or binocular simultaneous recording. The invention also describes scaling of the multifocal visual evoked potential (VEP) signals according to background electroencephalogram (EEG) levels, which reduces inter-individual variability.

BACKGROUND ART

The objective assessment of the visual field using multifocal stimulation has been reported recently (refs 1-7). Using different types of multifocal stimulus presentation (Sutter U.S. Pat. No. 4,846,567; Malov, International Patent Application No PCT/AU00/01483; and refs 14-17, the disclosures of which are hereby being incorporated by reference), stimulation of a large number of locations of the visual field can be performed simultaneously. Visually evoked cortical potentials (VEP) and electroretinograms (ERG) can be recorded from all areas of the field. For the VEP various electrode placements have been used. The best representation of the visual field was reported by the inventors with multichannel bipolar recordings (Klistorner and Graham, International Patent Application No. PCT/AU99/00340). Multifocal ERG recording has been performed with various electrodes (gold foil, DTL, Burian-Allen, gold lens). Good correlation was reported between the multifocal VEP and visual field loss in glaucoma (refs 2,5-7), and between the multifocal ERG and local retinal disease (ref 8), but not between the multifocal ERG and glaucoma (ref 9,10).

However, these recordings require a high resolution, large screen display (22 inch or larger), and subjects are required to sit close to the screen. The distance of the subject from the screen changes the area of field stimulated, and also changes the focal length and thus the required spectacle correction, so must be closely controlled during the recording. The CRT monitor also produces a large electromagnetic field which may affect the recordings when the subject is in close proximity to the screen. Recording is limited to one eye at the time, whereas with goggles it is possible to present a different stimulus to the two eyes at the same time. Therefore the concept of using a head mounted display provides a solution to these problems, and saves significantly on space requirements. It also allows for portability of the system. Binocular simultaneous multifocal recording reduces the recording time up to 50% by allowing two eyes to be tested simultaneously using different stimulus sequences for the two eyes.

A significant problem with multifocal VEP recordings has been the large inter-individual variability seen among the normal population, which limits the sensitivity of applying values from a normal data base when looking for small changes early in the disease process. A scaling algorithm has previously been reported by us (Klistomer & Graham, International patent application No. PCT/AU99/00340) which helped to reduce this variability. However, the scaling of VEP amplitudes according to background electroencephalogram levels as described in this patent has been found to be a superior technique for reducing inter-individual variability and increasing the sensitivity of the test.

DISCLOSURE OF THE INVENTION

The derivation of a functional map of the human visual field can be achieved from analysis of either multifocal VEP or ERG responses. The VEP responses tend to reflect losses at all stages of the visual pathway, whereas the ERG responses tend to correlate with local retinal disease. It has been demonstrated by Malov, International Patent Application No PCT/AU00/01483 that using a multifocal stimulus driven by a spread spectrum technique, (such that different parts of the visual field are stimulated by different random sequences), and by using appropriately placed recording electrodes on the scalp with multiple recording channels, that accurate maps of visual function can be recorded in the form of multifocal pattern VEPs. Disease states such as glaucoma or optic nerve disorders that cause blind spots in the vision (eg optic neuritis in multiple sclerosis) can be detected and mapped. Both amplitudes and latencies of the signals can be compared to normal reference values or compared between the two eyes of a subject.

We have found that a head mounted stereo display (eg virtual reality goggles) can be applied to these recording techniques, providing significant advantages. It reduces the space required in the laboratory or test area by removing the need for a large monitor. It makes the test potentially portable, and it standardises the distance to the display reducing problems of refraction, variable head position and thus area of field tested. It removes the problem of electromagnetic noise emanating from the screen when the subject sits close to the monitor. A head mounted stereo display has good patient acceptance, and both monocular or binocular recording can be performed.

Simultaneous binocular recording can be achieved with the application of the spread spectrum technique (Malov, International Patent Application No PCT/AU00/01483) and a head mounted stereo display to provide different pseudorandom stimulus patterns to the two eyes at the same time. The stimulus algorithm is divided into twice the number of segments and these can be distributed between the two eyes, still providing different stimulus sequences to each part of the field and with each subsequent run. The cross-correlations can derive VEP results from each eye independently, with minimal auto-correlation of the signals within or between eyes. This has the advantage of shortening the test time significantly. It also standardises conditions of the recording such that the two eyes are recorded under the same conditions in terms of the subject's visual attention and extraneous noise levels. This aids in the reliability of direct comparisons between eyes of an individual.

The invention thus provides a method and apparatus for objectively assessing the visual field using virtual reality goggles to present a multifocal stimulus and then recording of either retinal (ERG) or cortical (VEP) responses to that stimulus. It includes simultaneous binocular recording of the VEP, using different stimuli for the two eyes. It also includes a new scaling method to reduce inter-subject variability in the recorded multifocal VEP amplitudes by scaling the VEP response according to overall electroencephalogram activity.

A suitable head mounted stereo display is what is commonly known as virtual reality goggles. Other head mounted displays which are able to present a suitable stimulus which can generate a retinal or cortical response would also be appropriate.

"Virtual reality" is a term applied to the experience of an individual when viewing through a head-mounted display an image presented immediately before the eyes which has the appearance of being viewed at a distance from the eye. Different images can be presented to the two eyes to give a three dimensional effect.

It is a purpose of this invention to provide a method and apparatus for recording of responses from multiple parts of the visual field using virtual reality goggles, and thus provide a compact, portable system that is acceptable for the patient and clinician, and removes the need for close monitoring of recording distances from the viewing screen.

According to one aspect of this invention there is provided a method for objective electrophysiological assessment of visual function of at least one eye of a patient, which method comprises presenting a visual stimulus to at least one eye of the patient, recording at least one resultant response, selected from the group consisting of a retinal response and a cortical response, generated as a result of the presenting; analysing said response; and as a result of said analysing, forming a map of the visual function of the at least one eye of the patient.

Usually, the presenting of the visual stimulus is achieved by a head mounted display, in particular a head mounted stereo display such as a head mounted virtual reality stereo display.

According to another aspect of this invention there is provided a method for objective electrophysiological assessment of visual function, which method comprises placing a head-mounted stereo display for presenting a stimulus, on the head of a patient, placing electrodes on the scalp or in contact with the eye of said patient, connecting said head-mounted stereo display to a computer which generates an algorithm for driving said stimulus; generating said stimulus; recording the resultant retinal or cortical responses generated as a result of the stimulus; amplifying and analysing said responses; and as a result of said analysing, forming a map of the visual function.

According to a further aspect of this invention there is provided a method of identifying alpha-rhythm spikes or electrocardiogram signals in raw data by application of Fourier spectrum analysis. (It is important to identify these spikes prior to scaling since they may alert the operator to lack of visual attention of the patient.)

According to a still further aspect of this invention there is provided a system for electrophysiological assessment of visual function of at least one eye of a patient, comprising a head-mounted stereo display for presenting a stimulus to at least one eye of the patient; electrodes placed on the scalp or in contact with the eye; a computer which generates an algorithm for driving the stimulus; and a means for recording at least one resultant response, selected from the group consisting of a retinal response and a cortical response, generated as a result of presenting said stimulus; and means for recording the resultant retinal or cortical response; and software for analysing the retinal or cortical response to said stimulus.

According to another aspect of this invention there is provided a method for analysing at least one multifocal visual evoked potential recording from any mode of multifocal stimulation comprising scaling output from computer software according to overall spontaneous brain activity levels (ie. electroencephalogram levels) of a subject during the recording in order to minimise inter-subject variability. The EEG scaling is more reliable if a method for removing high alpha-rhythm signals or electrocardiogram contamination is employed when calculating the background EEG levels. The mode of multifocal stimulation includes conventional CRT or LCD monitors or plasma screens for example.

As mentioned above, the head-mounted stereo display suitable comprises virtual reality goggles. The head-mounted stereo display may be used to derive a signal from the cortical visual evoked potentials. It may also be used to derive an electroretinogram signal from the eye. This display shows any type of multifocal stimulation directly to the eye. The stimulus presented to the eye may be a flash stimulus or a pattern stimulus. The stimulus may vary in luminance, colour or stimulus duration to elicit visual responses. The head-mounted stereo display suitably uses a liquid crystal display or plasma screen, for example. The stimulus may be presented monocularly or binocularly. The same stimulus may be presented binocularly for simultaneously recording of signals from both eyes. Where different stimuli are presented to the two eyes, they may be simultaneously presented binocularly for simultaneous recording to signals from the two eyes. For analysis of multifocal visual evoked potential recordings, the results are scaled according to the overall spontaneous brain activity (i.e. electroencephalogram levels) of the subject during the recording to minimise variability.

The invention utilises multifocal stimulation techniques. Any multifocal stimulator (either existing equipment such as ObjectiVision, VERIS, Retiscan, or future systems) can be used to generate a stimulus which is then projected into virtual reality goggles using monocular or binocular displays. We have established that both the ObjectiVision and VERIS systems can be used in recording with virtual reality goggles. The stimulus can be diffuse (flash) or structured (pattern) and can vary in intensity, colour, size or temporal characteristics. Appropriate electrodes placed on the scalp for the VEP, or in the eye for the ERG, allow for recording of the electrophysiological response, which is then amplified by a conventional amplifier. Cross-correlation techniques (eg, Malov, International Patent Application No PCT/AU00/01483) allow for derivation of the signal from background noise. A topographical map of the responses can then be derived corresponding to the field of view of the subject. The output can displayed as a printout of results, and comparisons made with a normal data base of responses.

To reduce the inter-individual variability of the multifocal VEP recordings the inventors have applied a scaling factor based on background electroencephalogram (EEG) levels. Scaling of the VEP amplitude based on amplitude of spontaneous brain activity eliminates part of the variability between individuals caused by differences in conductivity of underlying tissues (eg bone, muscle, skin and subcutaneous fat). This also reduces the differences seen between males and females, since it is known that women have generally higher amplitude VEP signals when compared to men, presumably due to sex differences in tissue thickness and conductivity. Scaling according to EEG signals removes this difference, rendering final signals equivalent between the sexes. By reducing the range of variability between subjects it improves the sensitivity of the test for detecting abnormality.

BRIEF DESCRIPTION OF THE DRAWINGS

A number of embodiments of the present invention will now be described with reference to the drawings in which.

DESCRIPTION OF THE INVENTION

Figure 1:
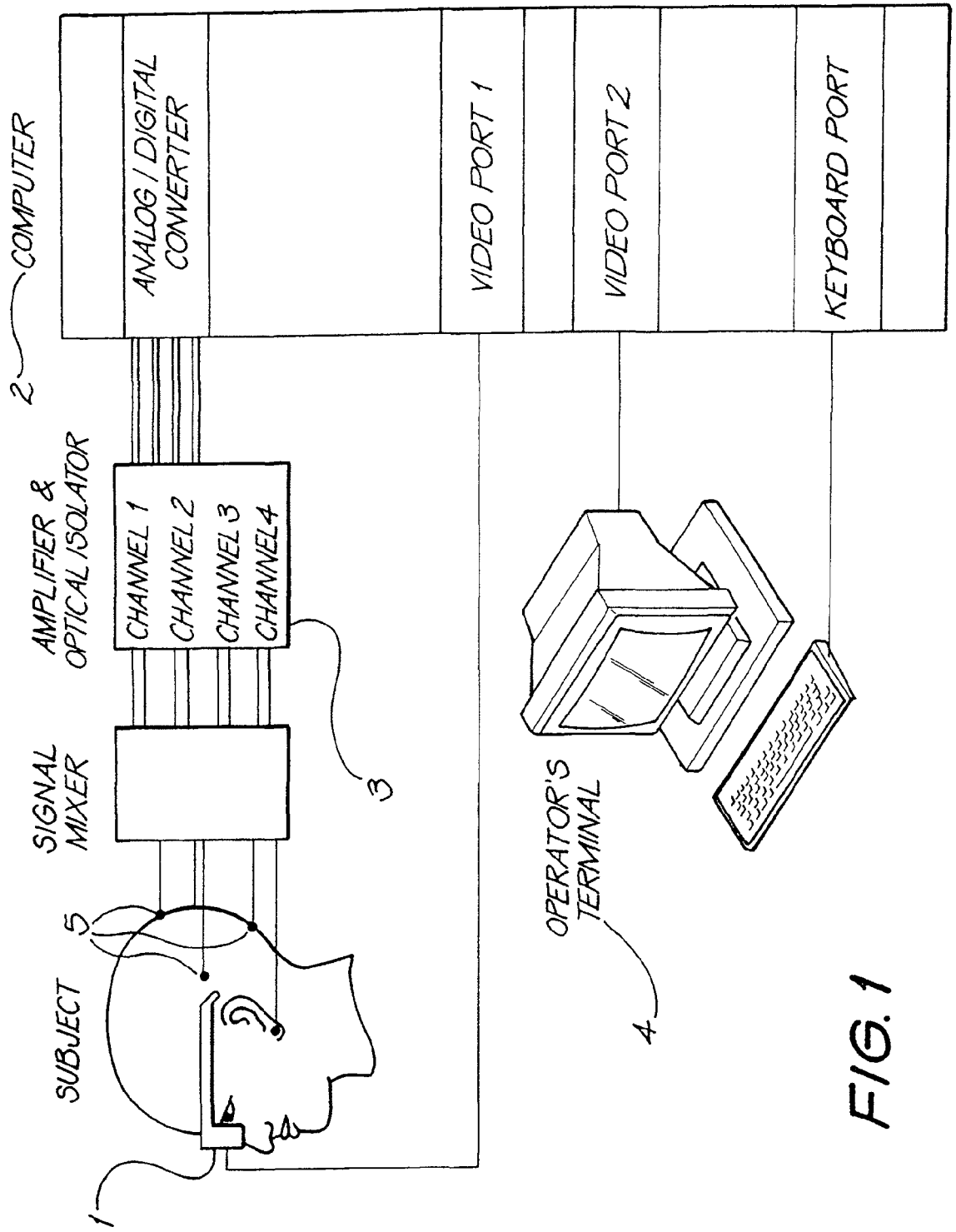
FIG. 1 is a schematic representation of the apparatus for VEP recording including virtual reality goggles.

FIG. 1 shows a schematic of the apparatus for VEP recording using virtual reality goggles (1), which present the display to the subject. The goggles are connected to a computer (2) with a linked video board that generates the multifocal stimulus. Recording electrodes on the scalp (5) and a ground reference electrode (shown on the earlobe), detect the VEP signal from one or more recording channels (in this case four channels are shown). The signals are conducted to an amplifier (3), before being processed by software for presentation on the operators display (4). Results can be compared for each eye, or between the two eyes of a subject, with respect to normal reference values.

Figure 2:
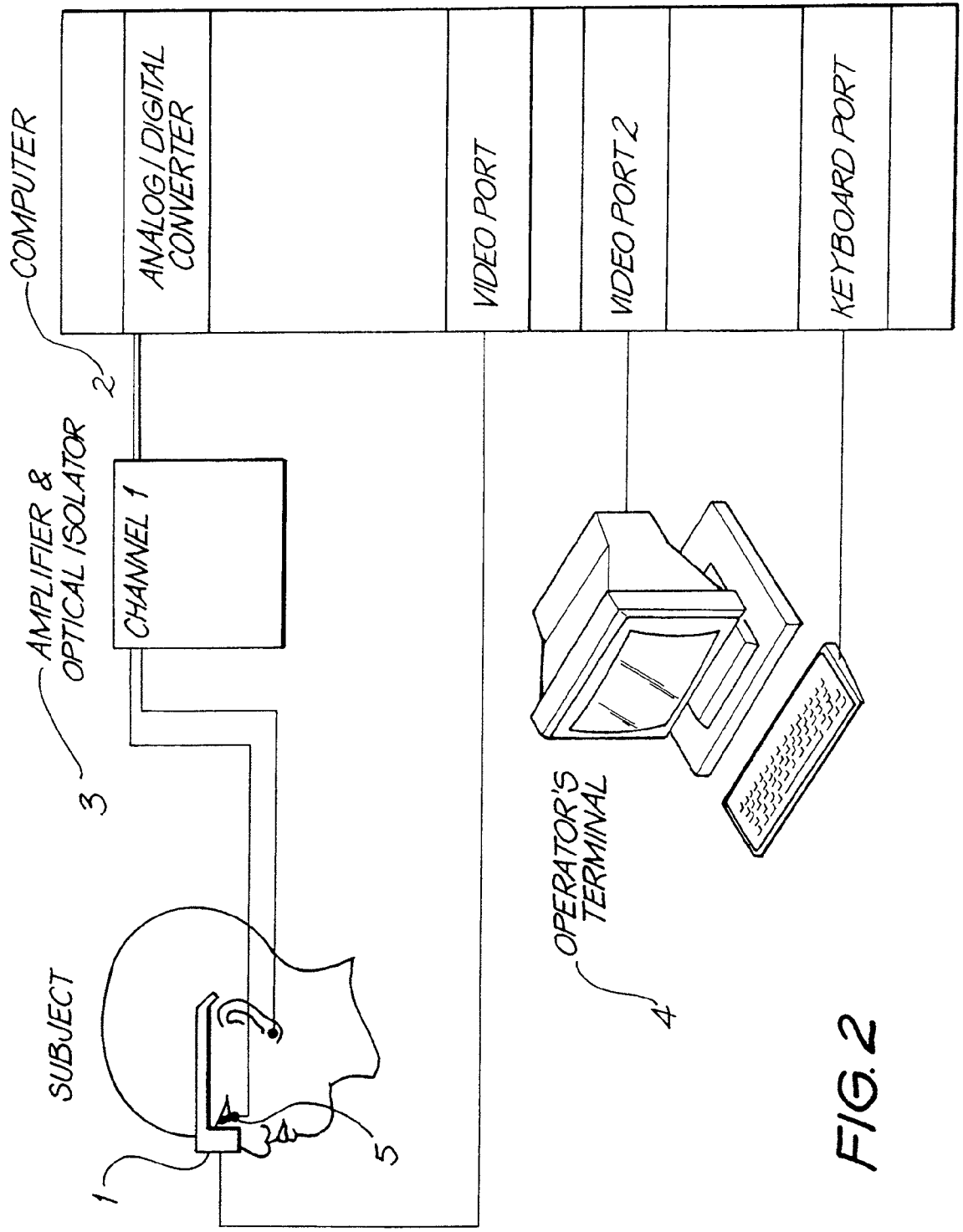
FIG. 2 is a schematic of the apparatus for ERG recording including virtual reality goggles.

FIG. 2 shows a schematic of the apparatus for multifocal ERG recording using virtual reality goggles (1). The set up is the same as in FIG. 1 except that the recording electrode is placed in contact with the eye or eyelid. A ground electrode is required (shown on the earlobe). Only one channel recording is required for the ERG.

Figure 3A:
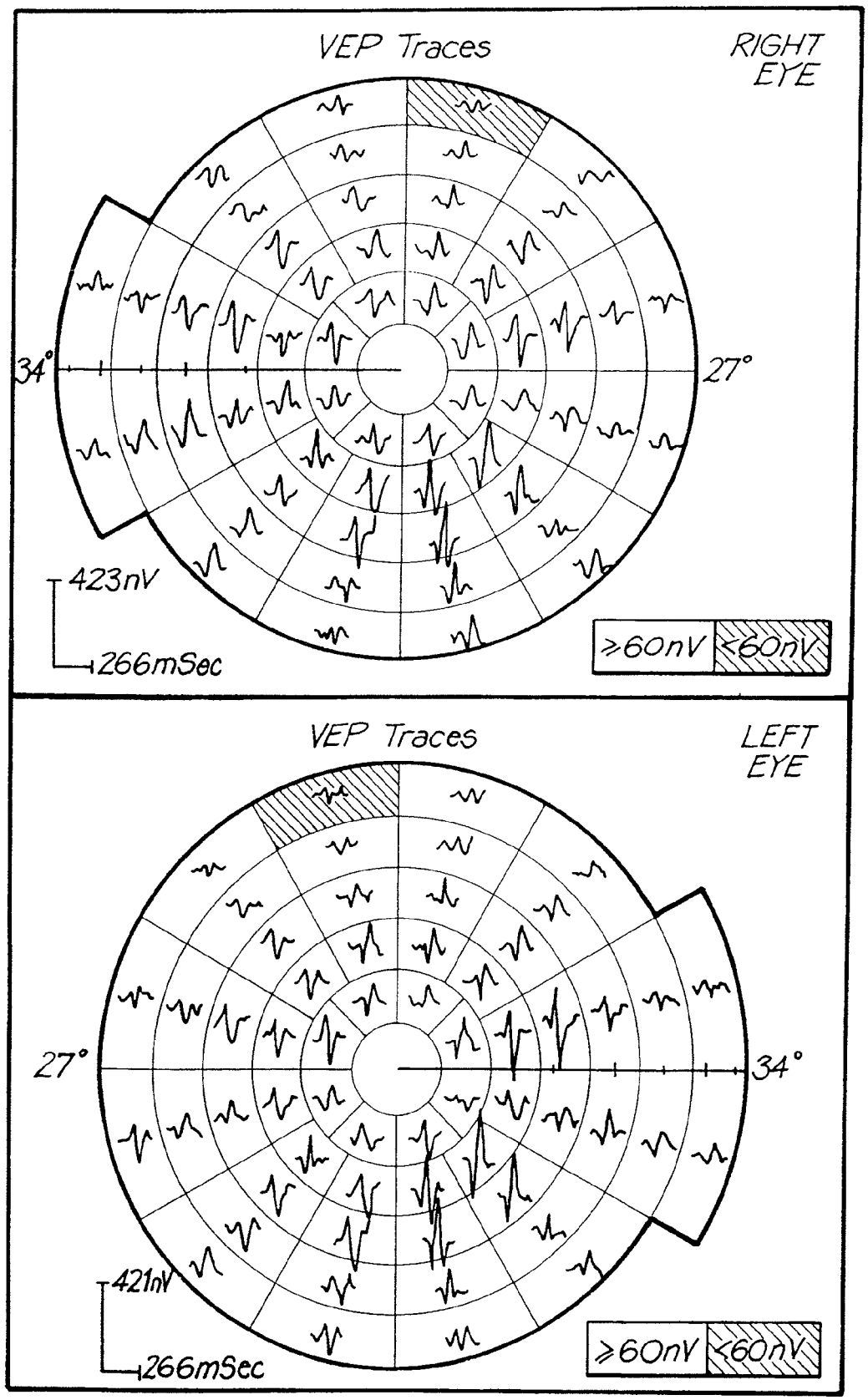
FIG. 3 is an example of a multifocal multichannel VEP recording from a normal subject using conventional screen (FIG. 3A) and goggles (FIG. 3B)
Figure 3B:
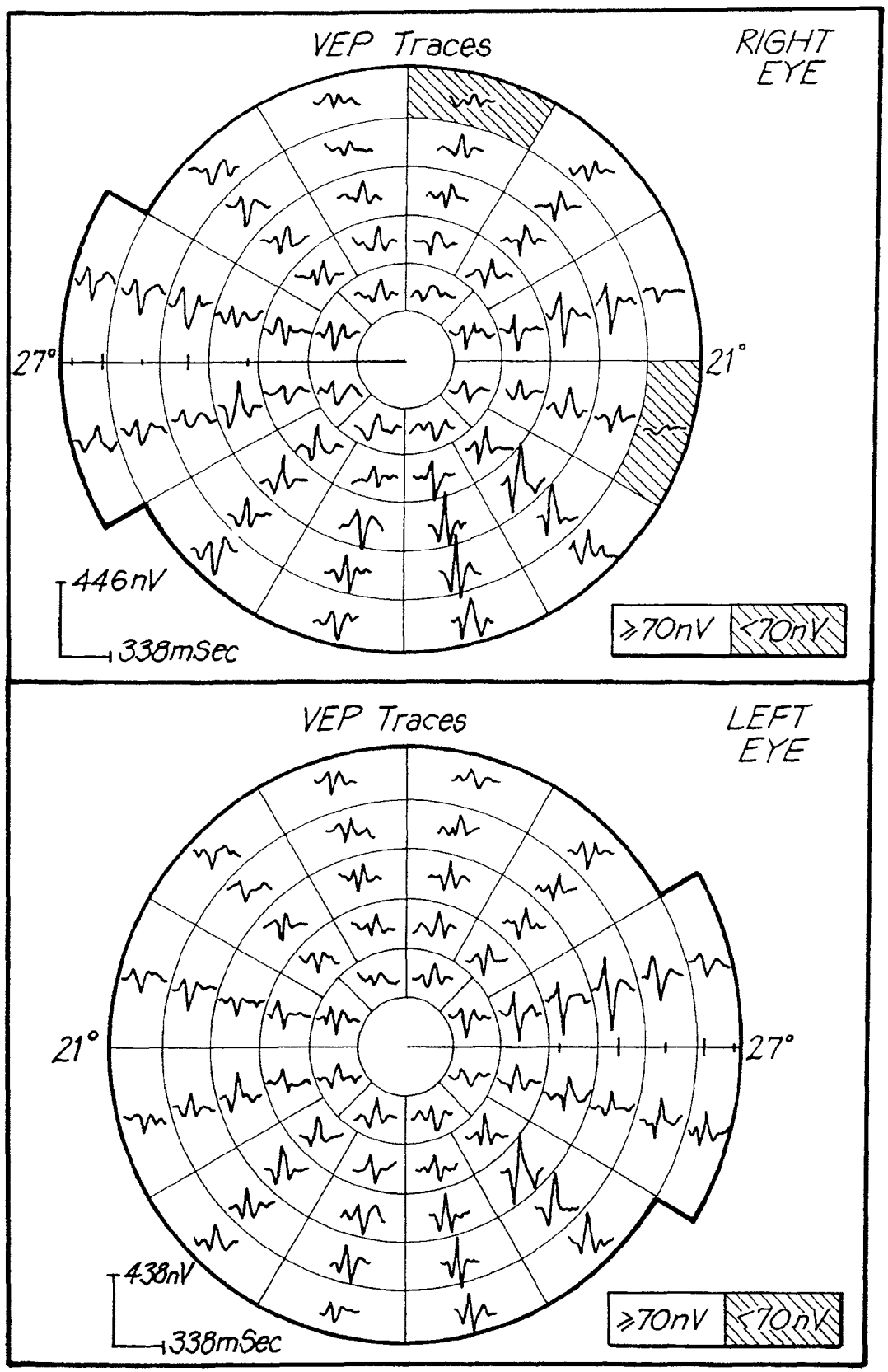

FIG. 3 is an example of a multifocal multichannel VEP recording from the right and left eye of a normal subject. FIG. 3A shows the responses achieved using a conventional screen (22 inch Hitachi monitor) to present the stimulus. A cortically scaled dartboard stimulus was generated with 60 different areas of pattern stimulation using the ObjectiVision perimeter. The trace array shown in the figure represents the responses generated from each part of the visual field tested out to 27 degrees of eccentricity temporally and 34 degrees nasally. For graphics purposes the central areas are relatively enlarged to show the raw VEP signal within that area. FIG. 3B shows a multifocal multichannel VEP recordings from the same normal subject as in FIG. 3A, recorded using virtual reality goggles to present the same stimulus instead of the conventional monitor. The same ObjectiVision system was used. The responses are of similar order of magnitude in the two techniques, although there is some variation in amplitude across the field. Due to the specifications of the goggles used, the display was limited to 21 degrees temporally and 27 degrees nasally.

Figure 4A:
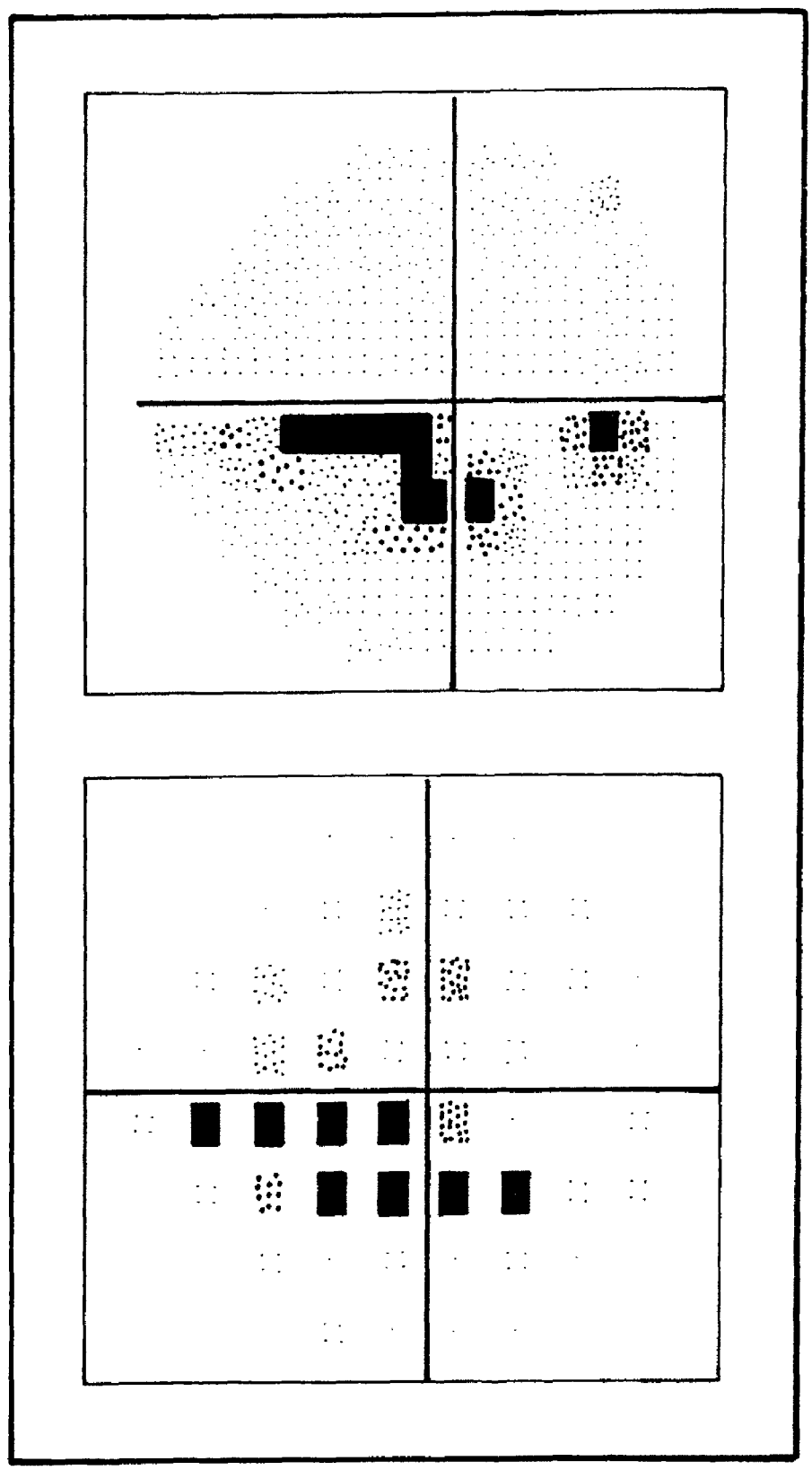
FIG. 4A shows the printout from a subjective Humphrey visual field test with a scotoma demonstrated in the inferior visual field of the right eye of a glaucoma patient.
Figure 4B:
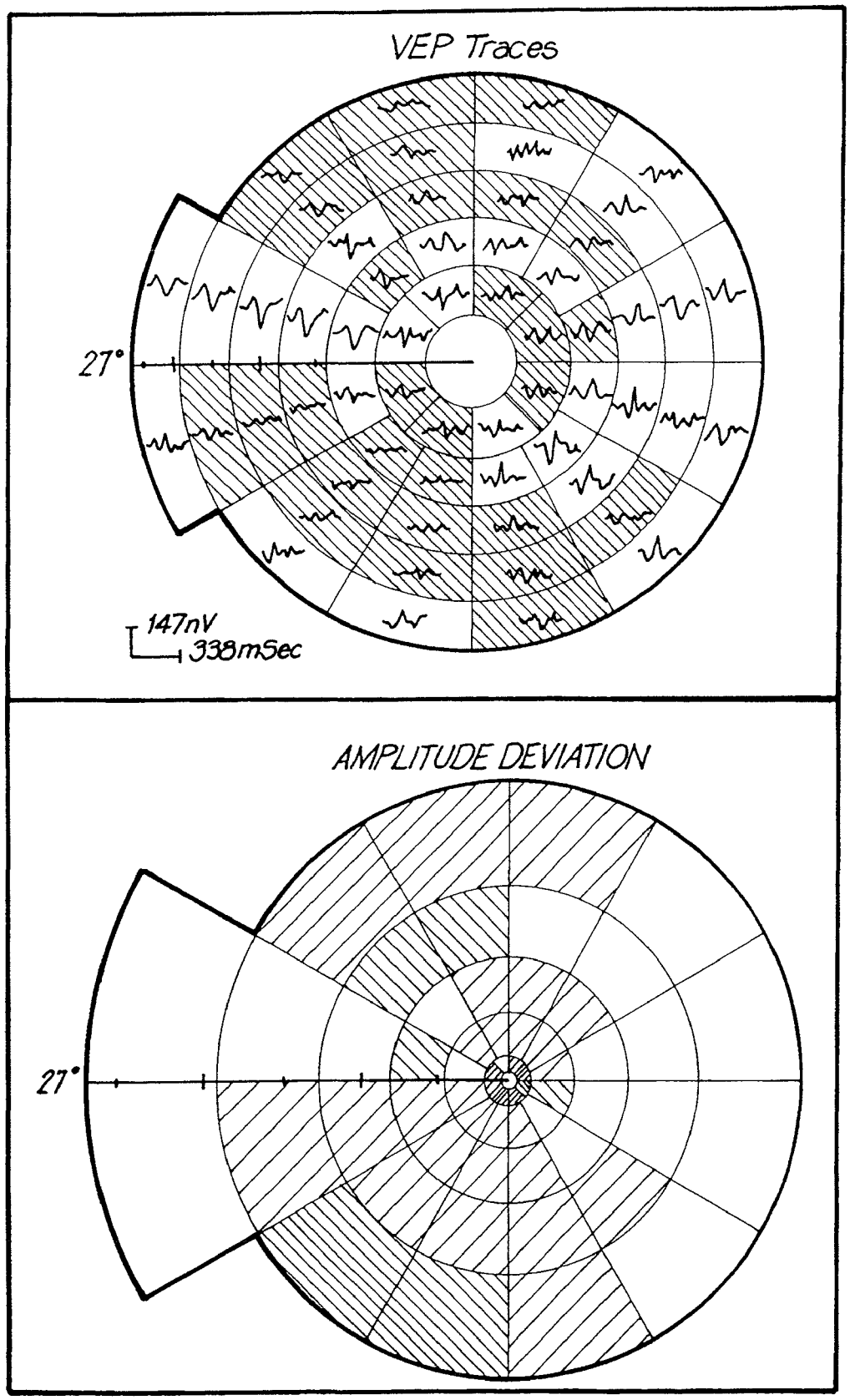
FIG. 4B shows a multifocal multichannel VEP recording using virtual reality goggles from the same eye as in FIG. 4A.

FIG. 4 provides a comparison between subjective perimetry findings and the objective VEP assessment of the visual field using virtual reality goggles. FIG. 4A shows the grayscale and pattern deviation printout from a subjective Humphrey visual field test of the right eye of a glaucoma patient. An inferior arcuate scotoma (blind spot) is shown in the visual field. FIG. 4B shows the multifocal multichannel VEP recording from the same eye as in FIG. 4A, recorded using virtual reality goggles. Analysis of the signals demonstrates loss of VEP responses corresponding to the inferior scotoma in FIG. 4A, with more extensive reductions in the superior field than seen on the Humphrey. The amplitude deviation plot shades areas according to probability of abnormality when compared to a reference range of normal values extrapolated from the conventional screen ObjectiVision system. This suggests that the technique is capable of detecting visual field loss in glaucoma, just as it is with the use of the conventional large screen. It may also demonstrate more significant glaucomatous damage than suspected on conventional Humphrey field testing. Five glaucoma patients have been tested with the virtual reality goggles and the scotomas were detected in all five cases.

Figure 5:
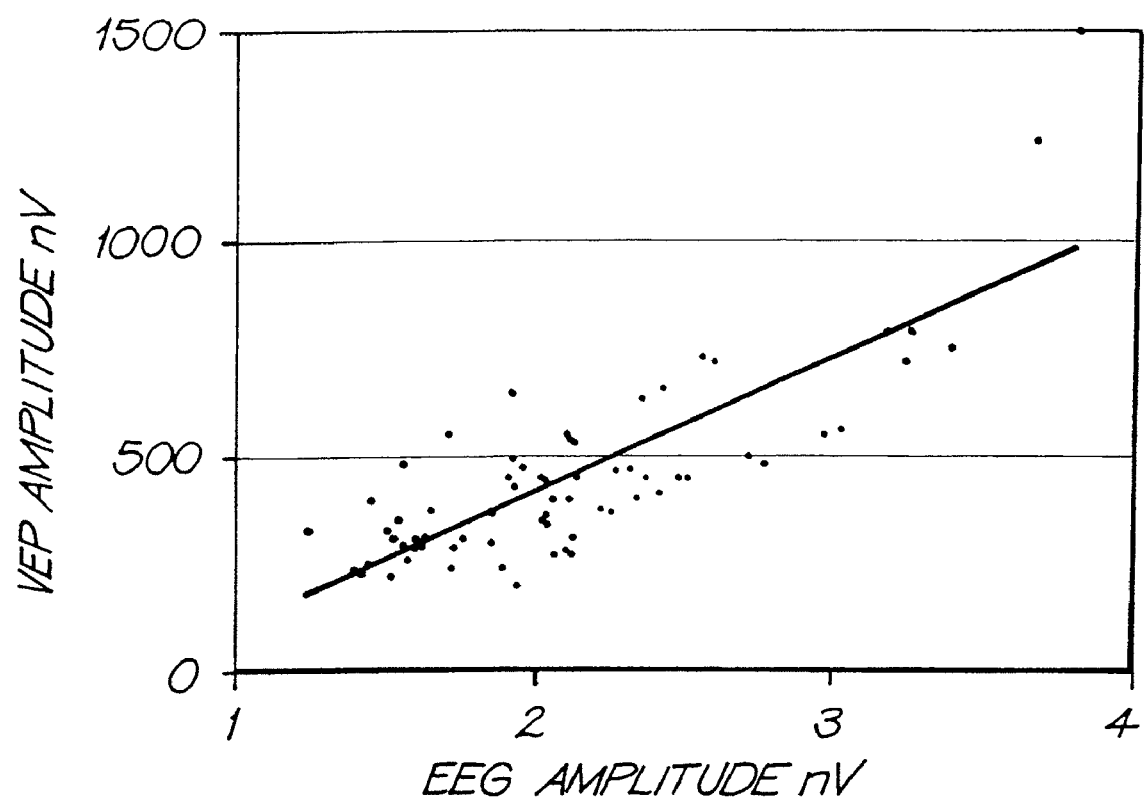
FIG. 5 shows the correlation between multifocal VEP amplitude and electroencephalogram (EEG) levels during recording.
Figure 6A:
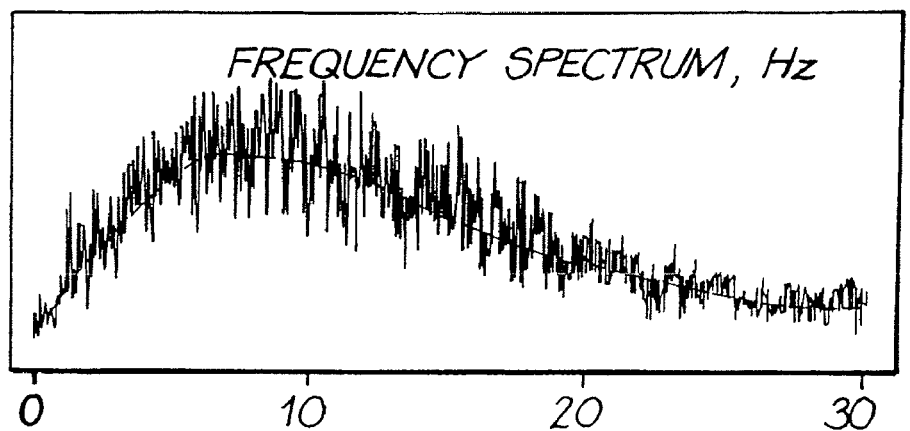
FIG. 6A shows an example of normal Fourier spectrum of EEG used for scaling VEP results.
Figure 6B:
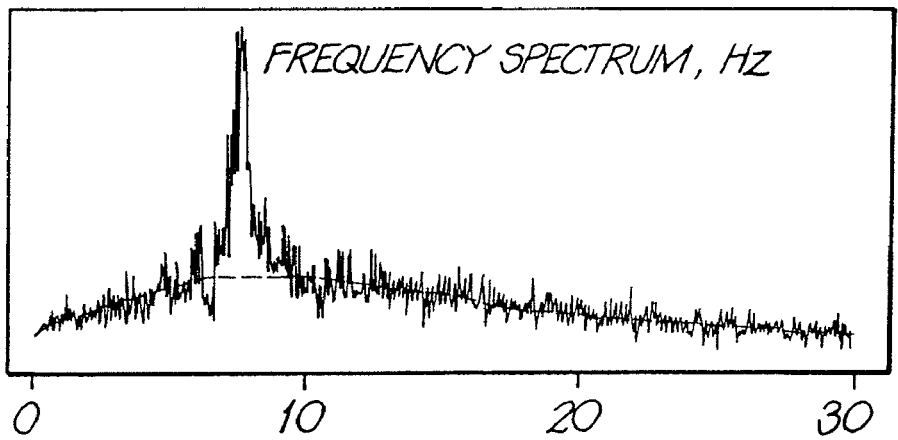
FIG. 6B shows a trace with strong alpha-rhythm activity around 8 Hz which must be removed before scaling (for example by using a polynomial algorithm)
Figure 6C:
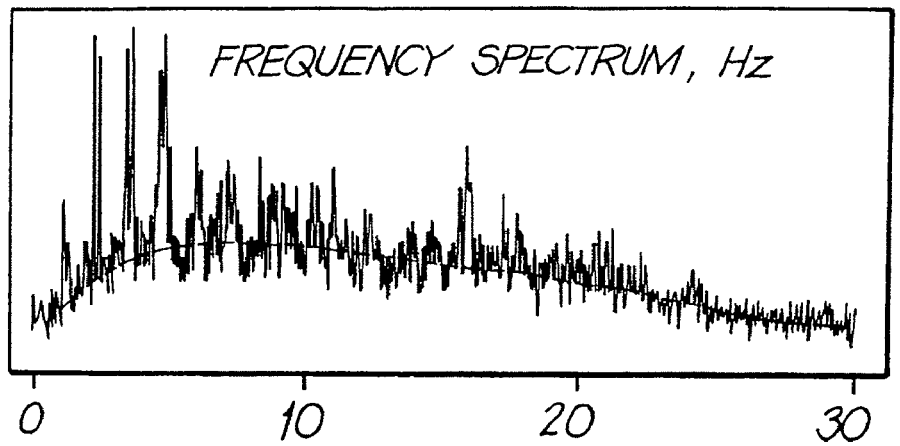
FIG. 6C shows rhythmic electrocardiogram spikes which also need to be excluded.

Examination of multifocal VEP data from normal subjects using conventional CRT monitors demonstrated that the amplitude of the multi-focal VEP is not age-dependant (contrary to most electrophysiology parameters, eg the pattern ERG). In fact, some elderly people produce VEP responses of higher amplitude. Individual variation in the thickness of the scalp or subcutaneous tissue may cause inter-individual differences in VEP amplitude due to variable impedance of bone and fat. Direct measurement of the thickness or impedance of these tissues is not currently practical. However, the impedance will also affect the amplitude of the spontaneous brain activity (EEG) in a similar fashion to the VEP. To confirm this we conducted a study using the ObjectiVision VEP perimeter of the correspondence between spontaneous EEG amplitude (99% confidence interval) and multifocal VEP amplitude (largest amplitude of a trace). The study included 34 normal subjects. The results demonstrated a strong correlation between the EEG amplitude and VEP (correlation coefficient r=0.81). The scatterplot for the correlation is shown in FIG. 5. An alternative method to measure background EEG activity is to calculate a Fourier power spectrum of the EEG.

Therefore, if the level of spontaneous EEG activity is calculated during the recording, it provides an indirect measure of the overall registration of brain signals for that individual for the electrode positions used. Whilst it is recognised that EEG amplitude is determined by many additional factors other than conductivity, it is proposed that scaling of an individual's VEP responses according to their EEG levels, relative to normal population EEG values, helps to reduce inter-individual VEP variability.

The EEG amplitude is approximately 1000× the amplitude of the VEP, so it is reasonable to assume that the VEP signals themselves will have little contribution to the raw EEG levels. In analysis of multifocal VEP recordings the EEG raw data is actually examined by cross-correlation techniques to extract the VEP signals. When recording from an individual, the overall level of the raw EEG (99% confidence interval) as recorded during each run of the VEP recording, can be used to provide an individual's scaling factor. The VEP extracted is then scaled by the EEG scaling factor.

The value of the technique of the invention of VEP scaling was confirmed by examining the data from 50 normals. The coefficient of variation for all 60 visual field test points had a mean value of 50.1%. When the results were scaled according to background EEG values the coefficient of variation for all 60 visual field test points was reduced to 28.2%.

By using EEG scaling, the sensitivity of the test was also improved. In a study of 60 glaucoma cases using the ObjectiVision system for multifocal VEP perimetry, several glaucoma cases were not flagged as abnormal using the unscaled data since the subjects had overall large signals compared with normal, even though focal relative reductions could be seen when examining the trace arrays. With the data scaled according to EEG levels however, these subjects were identified as having localised reductions in their VEP amplitudes and the scotomas were flagged appropriately.

The EEG raw data can contain a large component of alpha rhythm signals and also spikes of electrocardiogram signals. If these are not excluded from the scaling factor applied, then some subjects will have their data inadvertently scaled down lower than is appropriate. This can introduce false positive results in the VEP. One technique for rectifying this problem is to examine the raw signal by Fourier analysis and any alpha-rhythm spikes and electrocardiogram signals can be identified. These can then be excluded from the spectrum before calculating a scaling coefficient.

Therefore scaling of the VEP amplitude based on amplitude of spontaneous brain activity eliminates part of the variability between individuals caused by differences in conductivity of tissues. This technique has application in analysing multifocal VEP signals recorded with conventional CRT monitors, plasma screens, LCD screens, or with virtual reality goggles.

INDUSTRIAL APPLICABILITY

The method and system of this invention will find wide use in the medical field, specifically in the field of opthalmology.

The foregoing describes only some embodiments of the invention and modifications can be made thereto without departing from the scope of the invention.

REFERENCES

1. Baseler HA & Sutter EE. Vis Research 1997; 37(6):675-790
2. Klistomer AI, et al Invest Opthalmol Vis Sci 1998; 39(6): 937-950
3. Klistomer AI, et al Aust N Z J Opthalmol 1998; 26:91-94.
4. Graham SL, & Klistomer A. Aust N Z J Opthalmol 1998; 26:71-85
5. Graham SL, et al Surv Opthalmol 1999; 43 (Suppl1):s199-209
6. Graham SL & Klistorner A. Curr Opin Opthalmol 1999; 10:140-146.
7. Graham SL, et al J Glaucoma 2000; 9, 10-19
8. Kondo, M, et al Invest Opthalmol Vis Sci, 1995; 36:2146-2150
9. Vaegan & Buckland L. ANZ J Opthalmol 1996; 24(2):28-31
10. Johnson C A, et al J Glaucoma 2000; 9(AGS abstract):110
11. U.S. Pat. No. 4,846,567 (Sutter)
12. Graham S et al Vol 40 Invest Opthalmol Vis Sci, 1999, 40 (4) ARVO Abstract #318
13. U.S. Pat. No. 5,539,482 (James & Maddess)
14. Gold R IEEE Trans, 1967, V.IT-13 (4) 619-621
15. Sarwate & Pursley. Proc IEEE, 1980, Vol 68 (5) 593-619
16. Olsen et al IEEE Trans, 1982, V.IT-28(6) 858-864
17. Kamaletdinov B. Problems of Information Transmission, 1988, Vol 23 (2) 104-107
18. Klistorner PCT/AU99/00340

The invention claimed is:

1. A method for analysing at least one multifocal visual evoked potential response of at least two subjects, the at least one visual evoked potential response being induced by multifocal stimulation, wherein the stimulation is adapted to simultaneously stimulate different parts of the visual field of an eye of the subject such that different parts of the visual field are stimulated with random sequences of different timing or character, the method comprising:
   (a) for each subject, with electrodes placed on the scalp or in contact with the eye of each subject, simultaneously recording (A) the at least one visual evoked potential responses from each of the different parts of the visual field of the eye and (B) the subject's overall spontaneous brain activity levels;
   (b) for each subject, identifying, with a computer, the alpha rhythm component in the subject's overall spontaneous brain activity levels;
   (c) for each subject, removing, with said computer, the alpha rhythm component from the subject's overall spontaneous brain activity levels;
   (d) for each subject, calculating, with said computer, a corresponding scaling factor, the scaling factor being derived from the subject's overall spontaneous brain activity levels from which the component of alpha rhythm is identified and removed;
   (e) for each subject, scaling, with said computer, each subject's visual evoked potential response with said each subject's scaling factor such that the variability of the visual evoked potential responses induced by the multifocal stimulation between the at least two subjects is minimized; and
   (f) for the at least two subjects, storing or displaying said scaled visual evoked potential response.

2. The method of claim 1 wherein the alpha rhythm component in the subject's overall spontaneous brain activity levels is identified by wave component analysis.

3. The method of claim 2 wherein the alpha rhythm component in the subject's overall spontaneous brain activity levels is identified by Fourier analysis.

4. The method of claim 3 wherein the electrocardiogram spikes are identified by Fourier analysis of the subject's recorded overall spontaneous brain activity levels.

5. The method of claim 1 wherein step (b) comprises: for each subject, using Fourier power spectrum analysis to determine the subject's overall spontaneous brain activity levels, thereby to calculate a scaling factor.

6. The method of claim 1 wherein the multifocal stimulation stimulates responses from different parts of the visual field of both eyes of the subject and the responses from each of the different parts of the visual field for each eye are recorded simultaneously.

7. The method of any claim 1 further comprising the step of identifying and removing the effect of electrocardiogram spikes.

* * * * *